US011510839B2

(12) United States Patent
Ha et al.

(10) Patent No.: US 11,510,839 B2
(45) Date of Patent: Nov. 29, 2022

(54) WEARABLE APPARATUS FOR ASSISTANCE AND OPERATING METHOD THEREOF

(71) Applicant: Samsung Electronics Co., Ltd., Suwon-si (KR)

(72) Inventors: Taesin Ha, Seongnam-si (KR); Youngbo Shim, Seoul (KR); Byungjune Choi, Gunpo-si (KR)

(73) Assignee: Samsung Electronics Co., Ltd., Gyeonggi-Do (KR)

(*) Notice: Subject to any disclaimer, the term of this patent is extended or adjusted under 35 U.S.C. 154(b) by 391 days.

(21) Appl. No.: 15/854,173

(22) Filed: Dec. 26, 2017

(65) Prior Publication Data
US 2019/0046386 A1    Feb. 14, 2019

(30) Foreign Application Priority Data

Aug. 11, 2017    (KR) .................. 10-2017-0102103

(51) Int. Cl.
A61H 1/02       (2006.01)
B25J 9/00       (2006.01)
(Continued)

(52) U.S. Cl.
CPC .......... *A61H 1/0262* (2013.01); *A61F 2/604* (2013.01); *A61F 5/0102* (2013.01); *A61F 5/0125* (2013.01); *A61H 1/0237* (2013.01); *A61H 1/0244* (2013.01); *A61H 3/00* (2013.01); *B25J 9/0006* (2013.01); *A61B 5/1114* (2013.01);
(Continued)

(58) Field of Classification Search
CPC ........... A61H 1/0262; A61H 2201/165; A61H 3/00; B25J 9/0006; A41F 1/008; A61F 2002/5021; A61F 2002/502; A61F 2002/7862; A61F 2002/5016;
(Continued)

(56) References Cited

U.S. PATENT DOCUMENTS

| 5,893,367 A | 4/1999 | Dubats et al. |
| 8,221,339 B2 | 7/2012 | Hirata et al. |
| 8,652,075 B2 | 2/2014 | Takahashi et al. |
| 8,663,135 B2* | 3/2014 | Hirata ..................... A44B 11/28 182/3 |
| 9,662,262 B2* | 5/2017 | Hollander ............. B25J 9/0006 |
| 2011/0168485 A1* | 7/2011 | Hirata ..................... A44B 11/28 182/3 |

(Continued)

FOREIGN PATENT DOCUMENTS

JP    2009284919 A    12/2009
JP    5081740 B2    11/2012
(Continued)

OTHER PUBLICATIONS

Korean Office Action issued by Korean Intellectual Property Office (KIPO) dated Feb. 23, 2022 for the corresponding KR Patent Application No. 10-2017-0102103.

*Primary Examiner* — Bruce E Snow
(74) *Attorney, Agent, or Firm* — Harness, Dickey & Pierce, P.L.C.

(57) ABSTRACT

A wearable assistance apparatus is disclosed, wherein the wearable assistance apparatus may include a first frame configured to transfer a power in a first direction to assist a user, a second frame configured to transfer the power in a second direction to assist the user, a first wearing portion configured to urge the second frame towards the user in response to the first wearing portion being pulled in the first direction, and a second wearing portion configured to urge (Continued)

the first frame towards the user in response to the second wearing portion being pulled in the second direction.

10 Claims, 15 Drawing Sheets

(51) Int. Cl.
    *A61F 5/01* (2006.01)
    *A61H 3/00* (2006.01)
    *A61F 2/60* (2006.01)
    *A61B 5/11* (2006.01)
    *A61F 2/70* (2006.01)

(52) U.S. Cl.
    CPC .......... *A61F 2/70* (2013.01); *A61H 2201/165* (2013.01); *A61H 2201/1642* (2013.01); *A61H 2201/1652* (2013.01); *A61H 2201/503* (2013.01); *A61H 2201/5007* (2013.01); *A61H 2201/5053* (2013.01)

(58) Field of Classification Search
    CPC ............ A61F 2002/0155; A61F 5/0125; A61F 2/605; A61F 2/50
    See application file for complete search history.

(56) References Cited

U.S. PATENT DOCUMENTS

| | | | |
|---|---|---|---|
| 2015/0335515 A1* | 11/2015 | Lee | ........................ A61H 1/024 601/5 |
| 2016/0051435 A1 | 2/2016 | Ito et al. | |
| 2018/0200878 A1* | 7/2018 | Tsai | ..................... A61H 1/0262 |

FOREIGN PATENT DOCUMENTS

| | | |
|---|---|---|
| JP | 5161036-62 | 3/2013 |
| JP | 2013070784 A | 4/2013 |
| JP | 5878660 B2 | 3/2016 |
| JP | 5979703 B2 | 8/2016 |
| KR | 10-0966751 | 6/2010 |
| KR | 10-1233649 B1 | 2/2013 |
| KR | 10-2015-0134770 A | 12/2015 |

\* cited by examiner

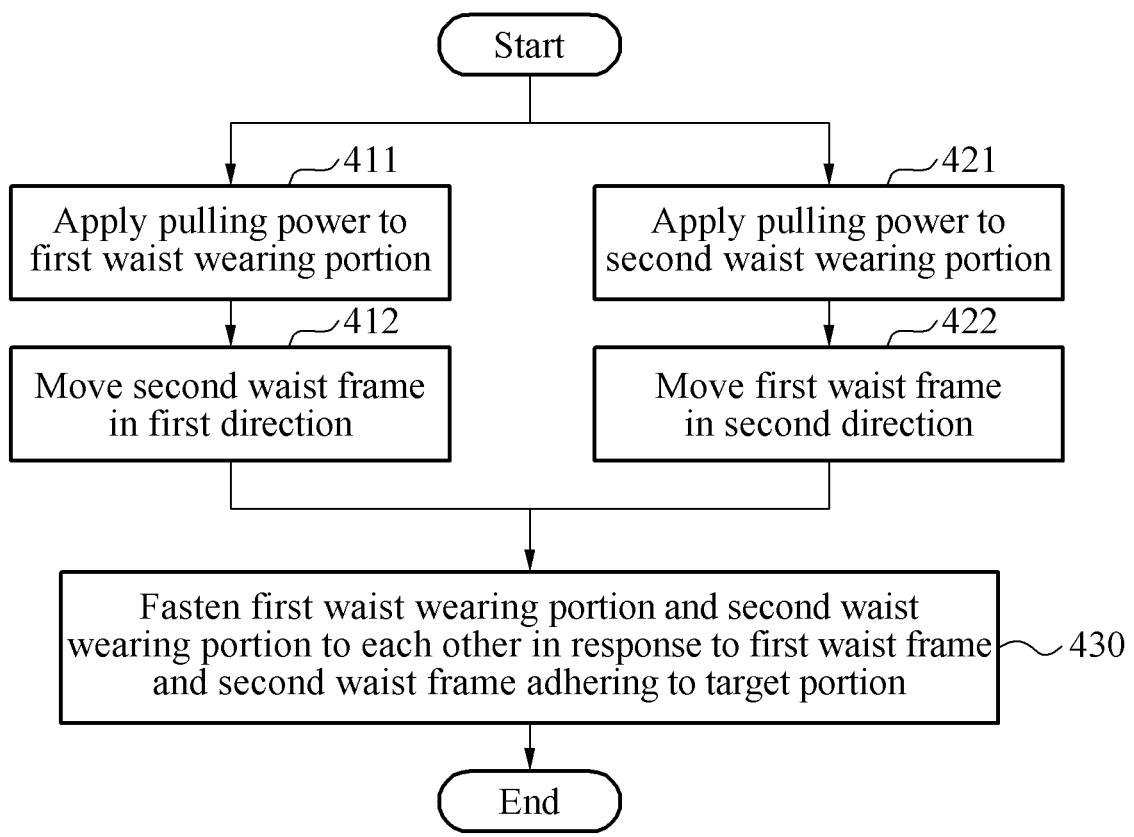

WEARABLE APPARATUS FOR ASSISTANCE AND OPERATING METHOD THEREOF

CROSS-REFERENCE TO RELATED APPLICATION

This application claims priority under 35 U.S.C. § 119 to Korean Patent Application No. 10-2017-0102103, filed on Aug. 11, 2017, in the Korean Intellectual Property Office, the entire contents of which are incorporated herein by reference in their entirety.

BACKGROUND

1. Field

At least one example embodiment relates to a wearable assistance apparatus and/or an operating method thereof.

2. Description of the Related Art

Today, a wearable assistance apparatus is used to provide assistance power to users who are experiencing discomfort in their daily life due to aging or injury. For example, wearable assistance apparatuses for increasing muscular strength to assist an elderly user or patients having joint problems to walk or stand with less effort or for increasing muscular strength of users are being developed.

SUMMARY

Some example embodiments relate to a wearable assistance apparatus.

In some example embodiments, the wearable assistance apparatus may include a first frame configured to transfer a power in a first direction to assist a user; a second frame configured to transfer the power in a second direction to assist the user; a first wearing portion configured to urge the second frame towards the user in response to the first wearing portion being pulled in the first direction; and a second wearing portion configured to urge the first frame towards the user in response to the second wearing portion being pulled in the second direction.

In some example embodiments, the wearable assistance apparatus may include a driving device configured to generate the power to assist the user; and a supporter configured to contact a target portion of the user to support the user.

In some example embodiments, the wearable assistance apparatus may include a guide configured to guide movement of at least one of the first frame and the second frame in a set direction.

In some example embodiments, the guide is configured to guide the at least one of the first frame or the second frame to linearly move in the set direction.

In some example embodiments, the guide comprises: a rail extendable along the set direction such that the at least one of the first frame and the second frame is configured to move along the rail.

In some example embodiments, the guide comprises: a guide block that forms a movement path along the set direction such that the at least one of the first frame and the second frame is configured to move along the movement path.

In some example embodiments, the set direction is orthogonal to a direction of the power generated by the driving device.

In some example embodiments, the wearable assistance apparatus may include a fastening portion configured to fix the first wearing portion to the second wearing portion such that the first frame and the second frame are fixed to a set target portion of the user in response to the first wearing portion being fastened to the second wearing portion.

In some example embodiments, the first frame is connected to a first end of the second wearing portion, and the second frame is connected to a first end of the first wearing portion.

In some example embodiments, the first wearing portion is configured to pass through a first hollow portion of the first frame, and the second wearing portion is configured to pass through a second hollow portion of the second frame.

In some example embodiments, the first wearing portion is configured to pass through the first hollow portion to transfer a first power to move the second frame, and the second wearing portion is configured to pass through the second hollow portion to transfer a second power to move the first frame.

Some other example embodiments relate to a wearable assistance apparatus.

In some example embodiments, the wearable assistance apparatus may include a supporter configured to contact a target portion of a user to support the user; a driving device configured to generate a power to assisting the user; a frame configured to transfer the power to the supporter; and a guide connected to the frame, the guide configured to guide the driving device to linearly move in a set direction.

In some example embodiments, the set direction is on a plane perpendicular to a central axis of a rotation power generated by the driving device.

In some example embodiments, the guide comprises: a rail extendable along the set direction such that the driving device is configured to move along the rail.

In some example embodiments, the guide further comprises: a moving member connected to the driving device and configured to move along the rail; at least one hole on the rail at a set distance; and a pin connected to the moving member and inserted into any one of the at least one hole to fix the driving device.

In some example embodiments, the guide comprises: a guide block configured to form a movement path along the set direction such that the driving device is configured to move along the movement path; a moving member connected to the driving device, the moving member configured to move along the movement path; and a stopper on the movement path.

In some example embodiments, the guide block includes a plurality of holes at a set distance, and the stopper is configured to penetrate one of the plurality of holes to fix the driving device.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 4 is a flowchart illustrating an operating method of a wearable assistance apparatus of FIG. 3;

DETAILED DESCRIPTION

Figure 1:
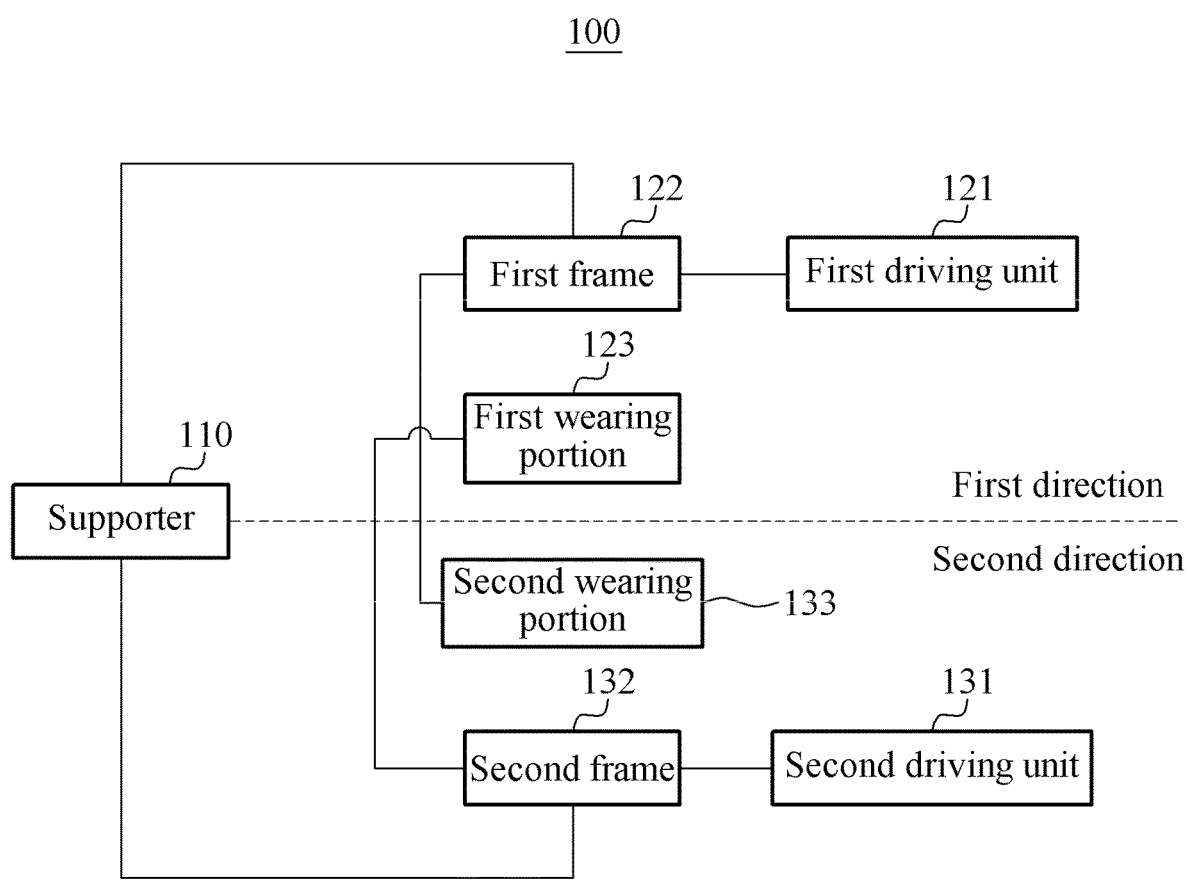
FIG. 1 is a block diagram illustrating a wearable assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 is a block diagram illustrating a wearable assistance apparatus according to at least one example embodiment.

Referring to FIG. 1, a wearable assistance apparatus 100 is worn by a user to assist a motion of the user. An example embodiment in which the wearable assistance apparatus 100 is worn by a human being is provided as an example only and should not be interpreted to limit or restrict the scope of other example embodiments. For example, the wearable assistance apparatus 100 may be worn by an animal, for example, a dog.

The wearable assistance apparatus includes a supporter 110, a first driving unit 121, a first frame 122, a first wearing portion 123, a second driving unit 131, a second frame 132, and a second wearing portion 133. The supporter 110 is in contact with a desired (or, alternatively, a predetermined) target portion to support the user. In an example, the supporter 110 is in contact with a back of a user to support the user. In another example, the supporter 110 is in contact with a knee or an elbow of a user to support the user.

The first driving unit 121 and the second driving unit 131 generate a power for assisting the user. As an example, which is not intended to be limiting, the first driving unit 121 and the second driving unit 131 may be provided as motor actuators. As another example, the first driving unit 121 and the second driving unit 131 may be provided as hydraulic actuators. In addition to the above-described examples, each of the first driving unit 121 and the second driving unit 131 may be provided as various devices for generating power.

Each of the first driving unit 121 and the second driving unit 131 may output the power for assisting a user in different directions based on the supporter 110. For example, the first driving unit 121 outputs a first power for assisting the user in a first direction. Also, the second driving unit 131 may output a second power for assisting the user in a second direction.

The first frame 122 may transfer the power for assisting the user in the first direction. In more detail, the first frame 122 is connected with the first driving unit 121 to fix a position of the first driving unit 121. In addition, the first frame 122 may transfer the first power from the first driving unit 121 to the supporter 110.

Similarly, the second frame 132 may transfer the power for assisting the user in the second direction. The second frame 132 is connected with the second driving unit 131 to fix a position of the second driving unit 131. The second frame 132 may transfer the second power from the second driving unit 131 to the supporter 110.

The first wearing portion 123 may be pulled from the first direction. The first wearing portion 123 allows the first frame 122 to adhere to the user based on a pulling power. The pulling power may occur in response to the user or a protector of the user pulling the first wearing portion 123 and the second wearing portion 133.

In a process in which the wearable assistance apparatus 100 is worn on a body of the user, the first frame 122 and the second frame 132 for transferring the power may move in a desired (or, alternatively, a predetermined) direction. In more detail, the wearable assistance apparatus 100 may include a cross-connection structure in which the first wearing portion 123 is pulled to move the second frame 132 and the second wearing portion 133 is pulled to move the first frame 122. Hereinafter, detailed descriptions of connection relationships and operation processes of the first wearing portion 123, the second wearing portion 133, the first frame 122, and the second frame 132 will be provided.

Figure 2:
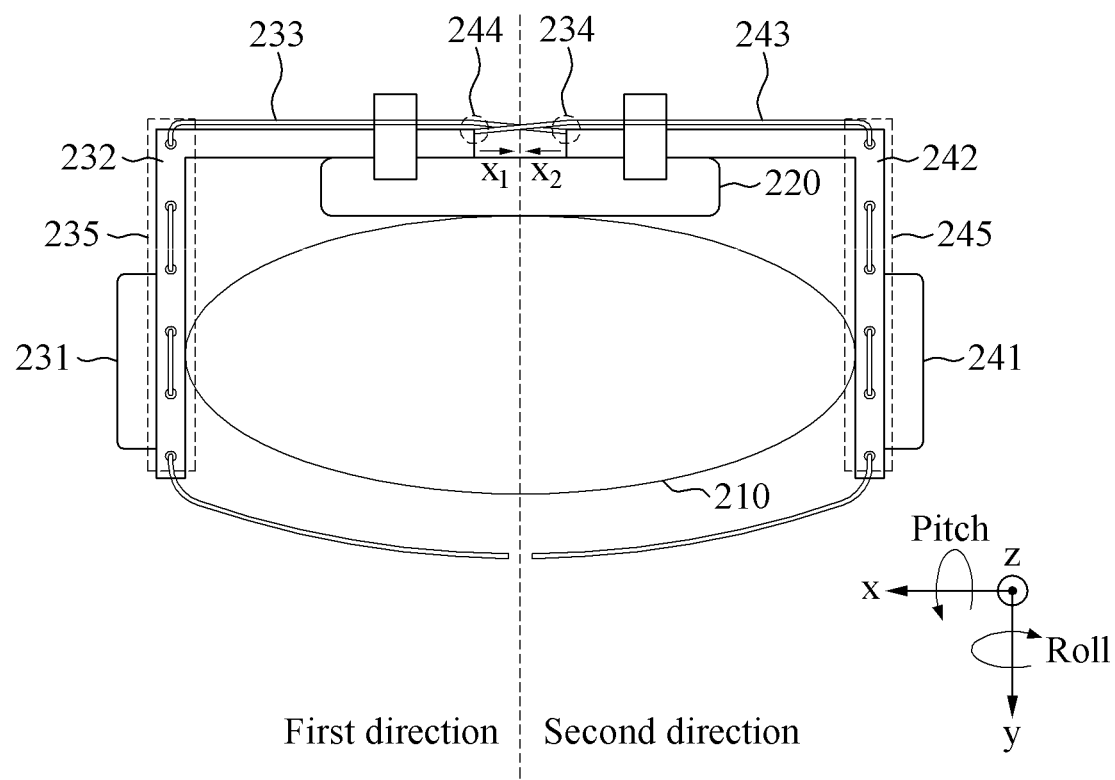
FIG. 2 is a top view of a wearable assistance apparatus of FIG. 1.

FIG. 2 is a top view of a wearable assistance apparatus of FIG. 1.

Referring to FIG. 2, a wearable assistance apparatus is worn on at least a body portion of a user. A supporter 220 is in contact with a desired (or, alternatively, a predetermined) target portion 210 to support the user. When the wearable assistance apparatus is provided as a hip joint assistance apparatus, the supporter 220 may support a back of the user. In addition, when the wearable assistance apparatus is provided as a knee assistance apparatus, the supporter 220 may support a knee of the user. Similarly, when the wearable assistance apparatus is provided as an elbow assistance apparatus, the supporter 220 may support an elbow of the user.

The wearable assistance apparatus may provide an assistance power in each of a first direction and a second direction of the user based the supporter 220. In the first direction, a first driving unit 231 may transfer a first power to the user through a first frame 232. The first driving unit 231 may generate a rotation power in a pitch direction as the first power based on an X-axis. Similarly, a second driving unit 241 may transfer a second power to the user through a second frame 242. The second driving unit 241 may generate the rotation power in the pitch direction as the second power based on an X-axis. When the wearable assistance apparatus is provided as the hip-joint assistance apparatus, the first power and the second power in the pitch direction may be provided for the user to assist a gait motion of the user.

A first wearing portion 233 in the first direction and a second wearing portion 243 in the second direction may be crossly connected to each of the first frame 232 and the second frame 242 based on the supporter 220. In more detail, the first wearing portion 233 may be connected to the second frame 242 present in the second direction. In addition, the first wearing portion 233 may be pulled from the first direction to move the second frame 242 in an $X_2$ direction such that the second frame 242 adheres to the target portion 210. One end 234 of the first wearing portion 233 may be connected to the second frame 242. The second wearing portion 243 may be connected to the first frame 232 present in the first direction. The second wearing portion 243 may be pulled from the second direction to move the first frame 232 in an $X_1$ direction such that the first frame 232 adheres to the target portion 210. One end 244 of the second wearing portion 243 may be connected to the first frame 232.

The first frame 232 includes a first hollow portion 235 through which the first wearing portion 233 passes. The first hollow portion 235 indicates a plurality of holes through which the first wearing portion 233 passes to transfer the pulling power to the second frame 242. The first wearing portion 233 may pass through the first hollow portion 235 to transfer a power for moving the second frame 242. Similarly, the second frame 242 includes a second hollow portion 245 through which the second wearing portion 243 passes. The second hollow portion 245 indicates a plurality of holes through which the second wearing portion 243 passes to transfer the pulling power to the first frame 232. The second wearing portion 243 may pass through the second hollow portion 245 to transfer a power for moving the first frame 232.

The wearable assistance apparatus may move the first frame 232 and the second frame 242 toward the desired (or, alternatively, the predetermined) target portion 210 through the first wearing portion 233 and the second wearing portion 243 that are crossly connected. In addition, a direction ($X_1$ direction or $X_2$ direction) in which each of the first frame 232 and the second frame 242 moves may correspond to a direction being orthogonal to the pitch direction for generating the rotation power by the first driving unit 231 and the second driving unit 241. Thus, positions of the first frame 232 and the second frame 242 may be fixed and remain unchanged due to the power generated by the first driving unit 231 and the second driving unit 241 in the wearable assistance apparatus.

Figure 3:
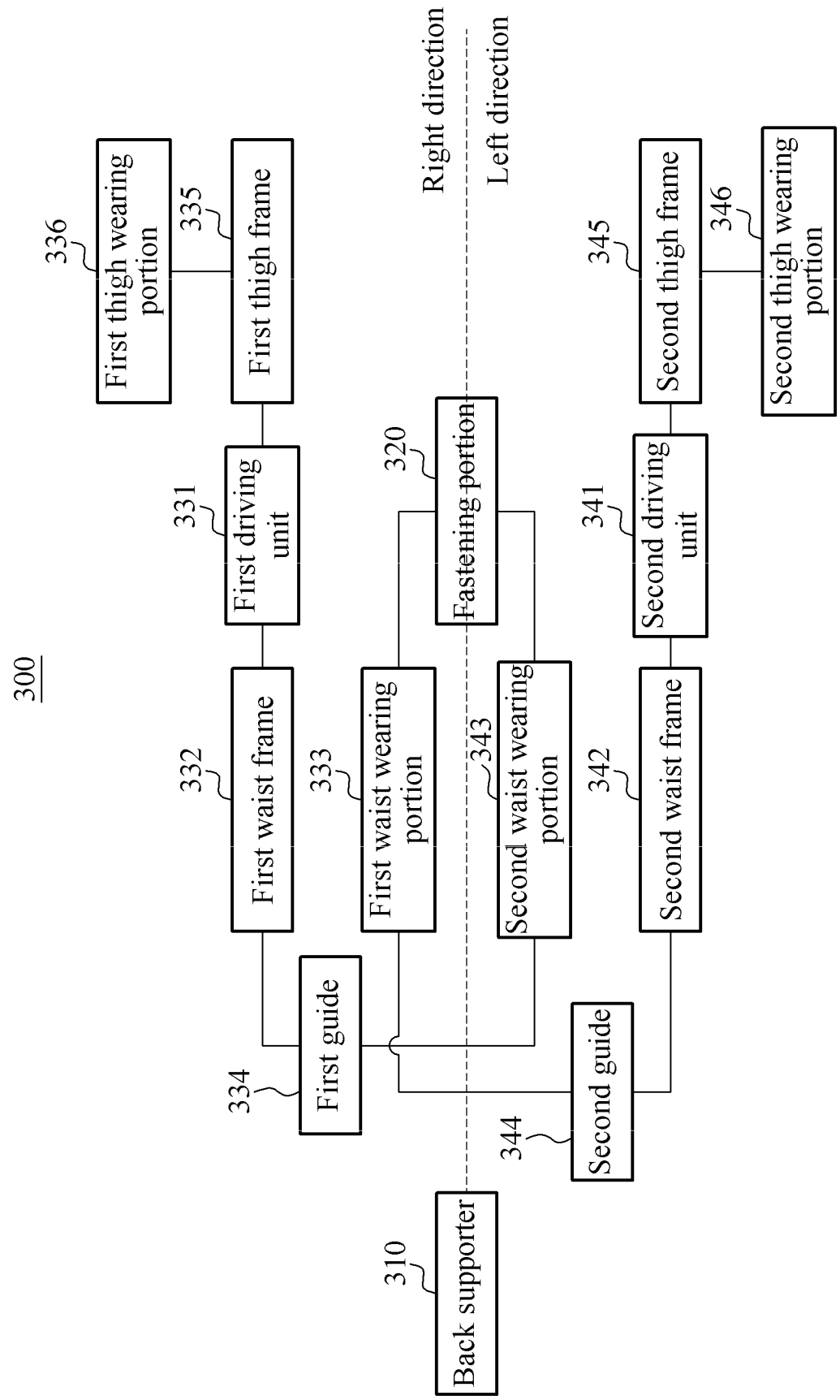
FIG. 3 is a block diagram illustrating a wearable assistance apparatus according to at least one example embodiment.

FIG. 3 is a block diagram illustrating a wearable assistance apparatus according to at least one example embodiment.

Referring to FIG. 3, FIG. 3 illustrates a wearable assistance apparatus 300 to be worn on a hip joint of a user to assist a gait motion. The wearable assistance apparatus 300 includes a back supporter 310, a fastening portion 320, a first driving unit 331, a first waist frame 332, a first waist wearing portion 333, a first guide 334, a first thigh frame 335, a first thigh wearing portion 336, a second driving unit 341, a second waist frame 342, a second waist wearing portion 343, a second guide 344, a second thigh frame 345, and a second thigh wearing portion 346.

The back supporter 310 is in contact with a back of the user to support the user. The back supporter 310 may transfer a power from the first waist frame 332 and the second waist frame 342 to the user.

The first driving unit 331 and the second driving unit 341 may generate the power for assisting the user and output the generated power. In detail, the first driving unit 331 may generate a first power in a right direction of the user to assist a gait of a right leg of the user. In addition, the second driving unit 341 may generate a second power in a left direction of the user to assist a gait of a left leg of the user.

The first waist frame 332 and the second waist frame 342 may fix the first driving unit 331 and the second driving unit 341 respectively, and transfer a power generated by each of the first driving unit 331 and the second driving unit 341 to the back supporter 310. For example, the first waist frame 332 and the second waist frame 342 are provided as rigid frames. In more detail, the first waist frame 332 may allow the user to adhere to the wearable assistance apparatus 300 in the right direction of the user. In addition, the second waist frame 342 may allow the user to adhere to the wearable assistance apparatus 300 in the left direction of the user.

The first waist wearing portion 333 and the second waist wearing portion 343 may cover a waist of the user. As an example, which is not intended to be limiting, the first waist wearing portion 333 and the second waist wearing portion 343 may be provided as width direction members, for example, belts, rubber bands, strings, wires, and chains. The first waist wearing portion 333 and the second waist wearing portion 343 may adherently fix the back supporter 310, the first waist frame 332, and the second waist frame 342 to a user body.

One end of the first waist wearing portion 333 is fixed and fastened to one end of the second waist wearing portion 343 through the fastening portion 320. In more detail, one end of the first waist wearing portion 333 may be fastened to one end of the second waist wearing portion 343 in an attachable state. For example, the fastening portion 320 is provided in a form of a hook-and-loop fastener or a buckle. The above example embodiment is provided as an example only and should not be interpreted to limit or restrict the scope of other example embodiments.

Another end of the first waist wearing portion 333 is connected to the second waist frame 342 through the second guide 344. In addition, another end of the second waist wearing portion 343 is connected to the first waist frame 332 through the first guide 334. Although the present disclosure describes that the first waist wearing portion 333 and the second waist wearing portion 343 are connected to the first waist frame 332 and the second waist frame 342 through the first guide 334 and the second guide 344, the first waist wearing portion 333 and the second waist wearing portion 343 are also connectable to the first waist frame 332 and the second waist frame 342 through one guide.

Each of the first guide 334 and the second guide 344 may guide the first waist frame 332 and the second waist frame 342 to move in a desired (or, alternatively, a predetermined) direction. In an example, each of the first guide 334 and the second guide 344 guides the first waist frame 332 and the second waist frame 342, respectively, to linearly move. In detail, each of the first guide 334 and the second guide 344 may guide the first waist frame 332 and the second waist frame 342, respectively, to freely move in a waist-width direction. Detailed descriptions of examples of the first guide 334 and the second guide 344 will be provided with reference to following drawings.

The first thigh frame 335 may be in contact with a right thigh of the user to transfer a power output from the first driving unit 331 to the right thigh. Similarly, the second thigh frame 345 may be in contact with a left thigh of the user to transfer a power output from the second driving unit 341 to the left thigh.

Each of the first thigh wearing portion 336 and the second thigh wearing portion 346 may transfer a power transferred from each of the first thigh frame 335 and the second thigh frame 345 to the thighs of the user.

In the wearable assistance apparatus 300, the first waist frame 332 may adhere to the user in the right direction through the first guide 334 and the second waist frame 342 may adhere to the user in the left direction through the second guide 344. The wearable assistance apparatus 300 may guide the first waist frame 332 and the second waist frame 342 to move in a direction being orthogonal to a direction of rotation power generated by the first driving unit 331 and the second driving unit 341 and thus, rotation axes of the first driving unit 331 and the second driving unit 341 may be consistently fixed.

FIG. 4 is a flowchart illustrating an operating method of a wearable assistance apparatus of FIG. 3.

Referring to FIGS. 3 and 4, in operation 411, a pulling power is applied to the first waist wearing portion 333. In more detail, the first waist wearing portion 333 is pulled from a right direction by a user. In another example, the first waist wearing portion 333 may be pulled from the right direction by a protector of the user, other than the user of the wearable assistance apparatus.

In operation 412, the second waist frame 342 moves in a desired (or, alternatively, a predetermined) first direction. The first direction corresponds to a right direction from which the first waist wearing portion 333 is pulled.

In operation 421, the pulling power is applied to the second waist wearing portion 343. The second waist wearing portion 343 may be pulled from a left direction by the user or the protector of the user. Subsequently, in operation 422, the first waist frame 332 moves in a predetermined second direction. The second direction corresponds to the left direction from which the second waist wearing portion 343 is pulled.

Although operation 421 is described after describing operation 411, this is only an example and should not be interpreted to limit or restrict the scope of other example embodiments. For example, the second waist wearing portion 343 present on the left is initially pulled and then the first waist wearing portion 333 present on the right is pulled. In addition, an operating method of the wearable assistance apparatus may include a method of pulling the first waist wearing portion 333 and the second waist wearing portion 343 at the same time.

In operation 430, the first waist frame 332 and the second waist frame 342 adhere to a target portion of the user. In this case, the first waist wearing portion 333 and the second waist wearing portion 343 may be fastened to each other. For example, the first waist wearing portion 333 and the second waist wearing portion 343 may be fastened to each other through a hole formed on one end of the first waist wearing portion 333 and a pin formed on one end of the second waist wearing portion 343.

In response to the first waist wearing portion 333 and the second waist wearing portion 343 being fastened to each other, the first waist frame 332 and the second waist frame 342 may not move further and may be fixed to the desired (or, alternatively, the predetermined) target portion. In more detail, each of the first waist frame 332 and the second waist frame 342 may adhere to a body of the user such that the first waist frame 332 and the second waist frame 342 may be unable to move in an inward direction, and a fastening portion for fixing the first waist wearing portion 333 and the second waist wearing portion 343 may prevent movements of the first waist frame 332 and the second waist frame 342 in an outward direction.

When the wearable assistance apparatus is worn, the waist frames 332, 342 for transferring power may move to correspond to a size of body of the user and may be fitted into the user, such that waist wearing portions 333, 343 are fixed to a desired (or, alternatively, a predetermined) target portion without moving further when the waist wearing portions 333, 343 are fastened to each other and the wearing of the wearable assistance apparatus is complete and the driving units 331, 341 may stably transfer an assistance power.

Figure 5A:
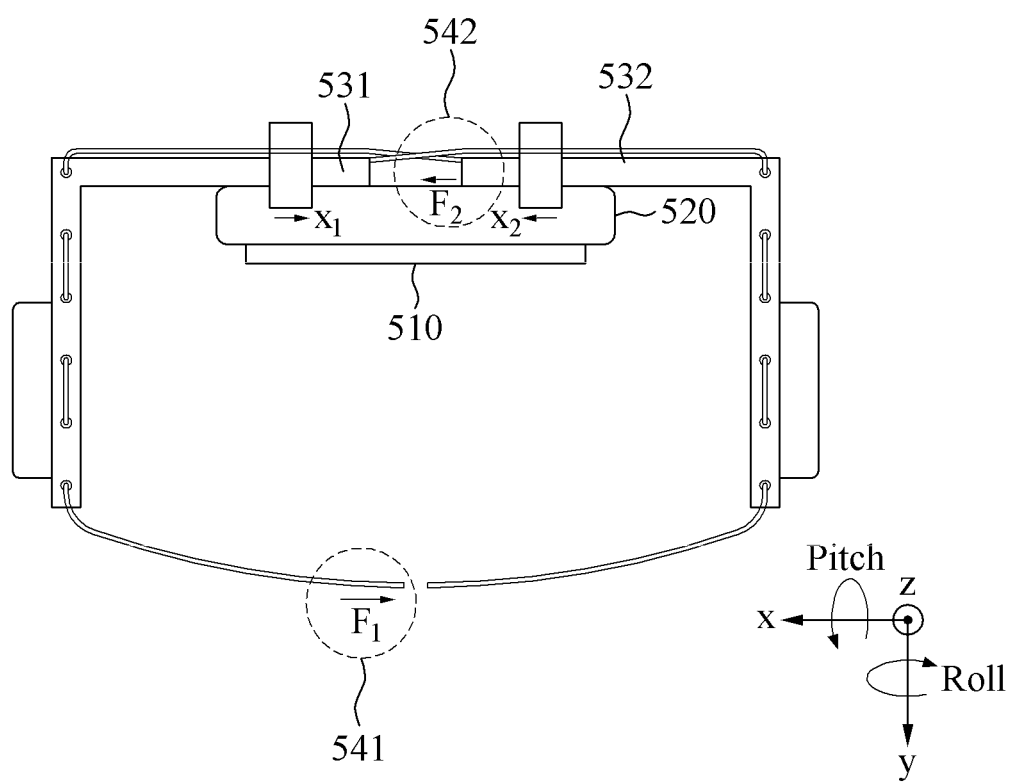
FIG. 5A is a top view of a guide according to at least one example embodiment.

FIG. 5A is a top view of a guide according to at least one example embodiment.

Referring to FIG. 5A, a guide 520 for guiding each of a first frame 531 and a second frame 532 to move in a predetermined direction may be disposed on a supporter 510. For example, when the supporter 510 adheres to a back of the user, the guide 520 may guide each of the first frame 531 and the second frame 532 to move in a waist-width direction of the user.

Although FIG. 5A illustrates that the supporter 510 adheres to a back of the user for ease of description, the guide may also operate even when the supporter 510 adheres to other body portions, for example, an elbow or a knee.

In response to a first pulling power $F_1$ 541 being applied to a first wearing portion from the user or a protector of the user, a second pulling power $F_2$ 542 is applied to the second frame 532. Thus, the second frame 532 may move in an $X_2$ direction, that is, the waist-width direction. In detail, the second frame 532 may move in the $X_2$ direction, that is, a direction of the second pulling power $F_2$ 542, determined through a movement path provided by the guide 520. Similarly, although not described in FIG. 5A, the first frame 531 may also move in an $X_1$ direction, that is, the waist-width direction of the user even when a pulling power is applied to the second wearing portion. Hereinafter, implementation examples of the guide 520 are provided with reference to following drawings.

Figure 5B:
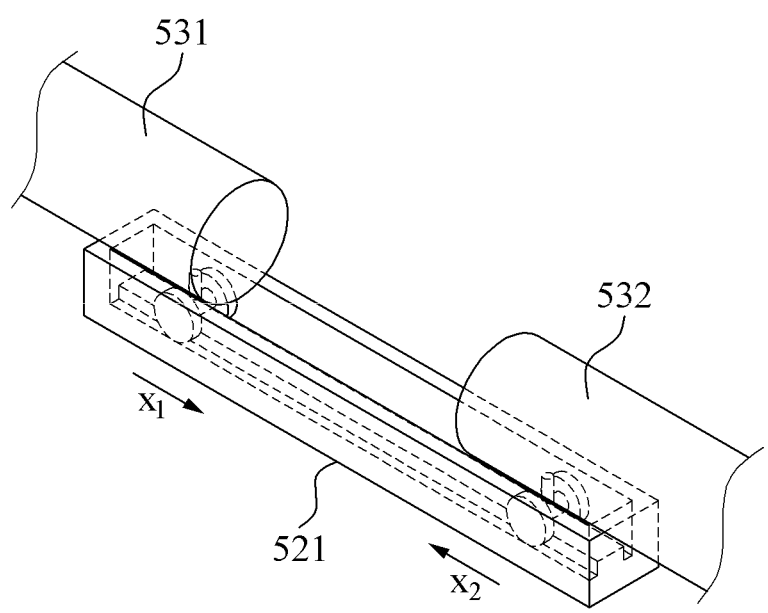
FIG. 5B is a perspective view of a guide according to at least one example embodiment.

FIG. 5B is a perspective view of a guide according to at least one example embodiment. A guide 521 includes a rail extendable along a desired (or, alternatively, a predetermined) direction. The desired (or, alternatively, the predetermined) direction may indicate an axial direction (X-axial direction) of a rotation power generated by a driving unit. At least one of the first frame 531 or the second frame 532 may move along the rail included in the guide 521. The guide 521 may include wheels disposed under each of the first frame 531 and the second frame 532 that move on the rail.

A pulling power to be applied to a first wearing portion may move the second frame 532 along the rail in an $X_2$ direction. In addition, a pulling power to be applied to a second wearing portion may move the first frame 531 along the rail in an $X_1$ direction.

Figure 5C:
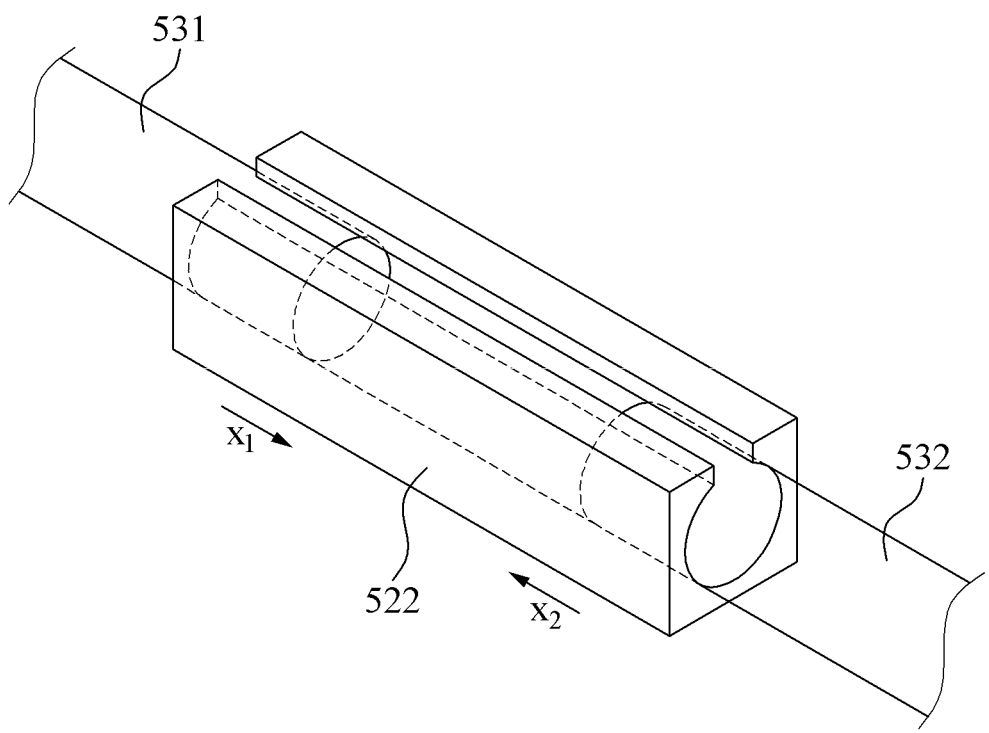
FIG. 5C is a perspective view of a guide according to at least one example embodiment.

FIG. 5C is a perspective view of a guide according to at least one example embodiment. A guide 522 includes a guide block that forms a movement path along a desired (or, alternatively, a predetermined) direction. The desired (or, alternatively, the predetermined) direction may indicate an axial direction (X-axial direction) of a rotation power generated by a driving unit. At least one of the first frame 531 or the second frame 532 may move along the movement path provided by the guide 522.

Similarly, a pulling power to be applied to a first wearing portion may move the second frame 532 along the movement path in an $X_2$ direction. In addition, a pulling power to be applied to a second wearing portion may move the first frame 531 along the movement path in an $X_1$ direction.

The above example embodiments of FIGS. 5B and 5C are provided as examples only and should not be interpreted to limit or restrict the scope of other example embodiments.

Figure 6:
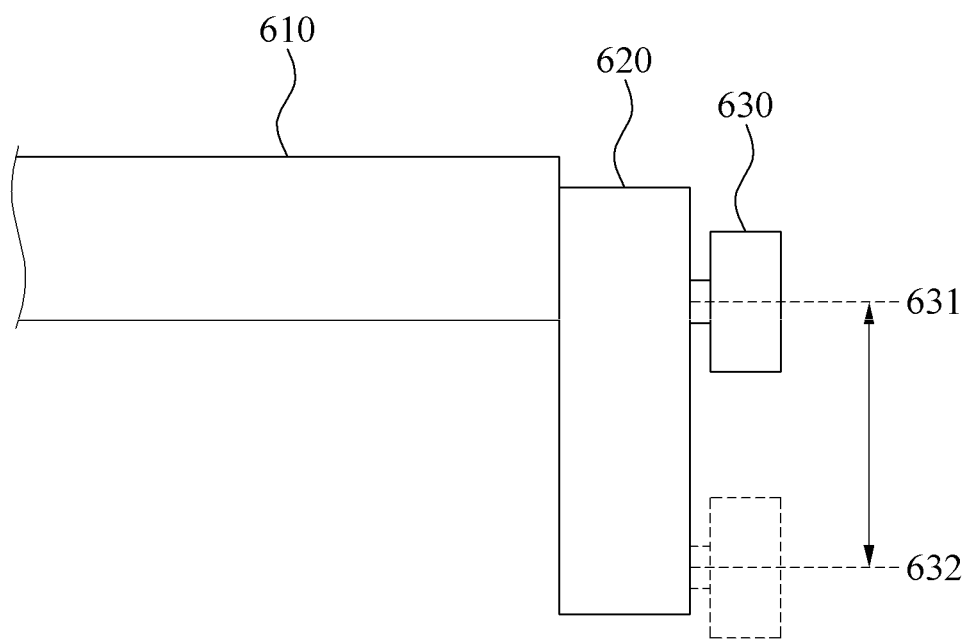
FIG. 6 illustrates a wearable assistance apparatus according to at least one example embodiment.

FIG. 6 illustrates a wearable assistance apparatus according to at least one example embodiment.

Referring to FIG. 6, the wearable assistance apparatus includes a frame 610, a guide 620, and a driving unit 630. The frame 610 transfers a power generated by the driving unit 630 to a supporter. The guide 620 is connected to the frame 610 and guides the driving unit 630 to linearly move in a desired (or, alternatively, a predetermined) direction. In more detail, the guide 620 is disposed between the frame 610 and the driving unit 630. The driving unit 630 may freely move from a first position 631 to a second position 632 through the guide 620. In more detail, the wearable assistance apparatus may adjust a position of the driving unit 630 based on size of a user body. The wearable assistance apparatus may adjust an axial direction of a rotation power output by the driving unit 630 to correspond to various body sizes, for example, a waist width, a hip height, a stomach thickness, and a leg thickness, such that the axial direction corresponds to a joint of the user. Hereinafter, a process of adjusting the position of the driving unit 630 based on the guide 620 is described with reference to more detailed drawings.

Figure 7A:
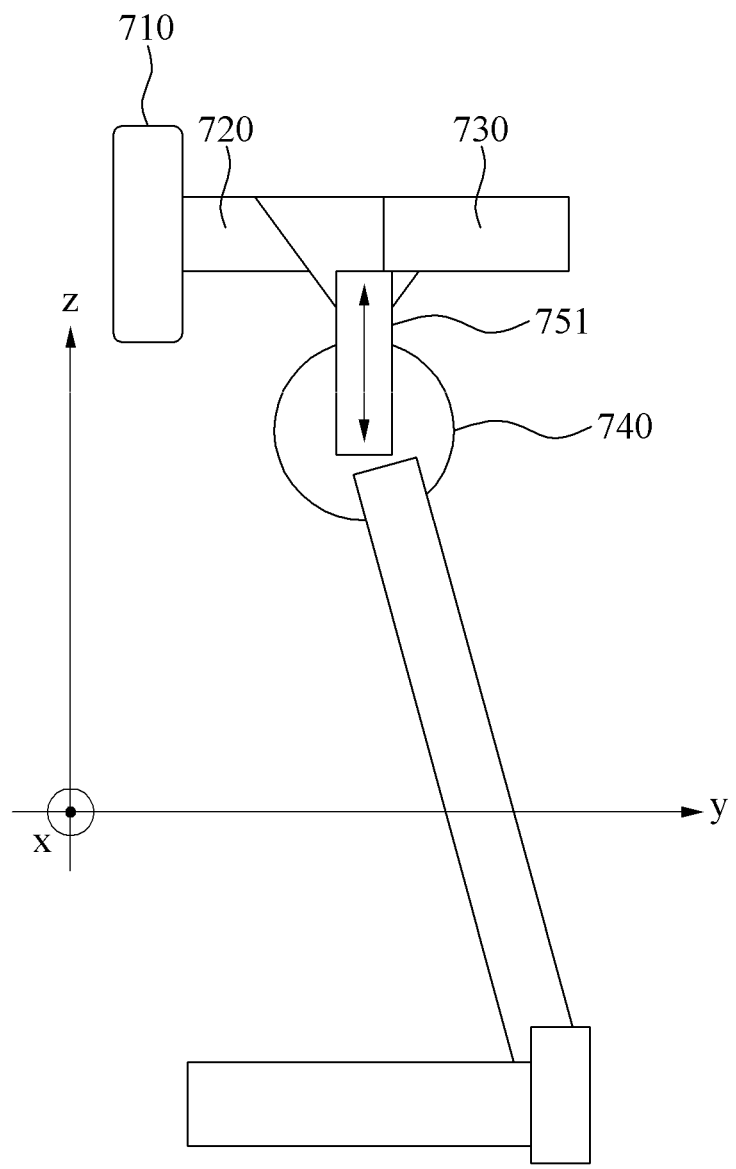
FIG. 7A is a side view of a wearable assistance apparatus for adjusting a position of a driving unit according to at least one example embodiment.

FIG. 7A is a side view of an example of a wearable assistance apparatus for adjusting a position of a driving unit.

Referring to FIG. 7A, FIG. 7A illustrates the wearable assistance apparatus to be worn on a hip joint of a user. The wearable assistance apparatus includes a back supporter 710, a waist frame 720, a waist wearing portion 730, a driving unit 740, and a first guide 751. The descriptions provided with reference to FIG. 3 are also applicable to the back supporter 710, the waist frame 720, the waist wearing portion 730, and the driving unit 740. Thus, duplicated descriptions will be omitted for conciseness.

The first guide 751 is connected to the waist frame 720 and guides the driving unit 740 to linearly move in a desired (or, alternatively, a predetermined) direction. For example, the predetermined direction indicates a Z-axial direction (upward direction and downward direction) based on a user body. The driving unit 740 may have a freedom degree of a movement from an upward direction to a downward direction through the first guide 751. Thus, the wearable assistance apparatus may adjust a position of a driving unit in a direction of a height of the user corresponding to a size of the user body.

Figure 7B:
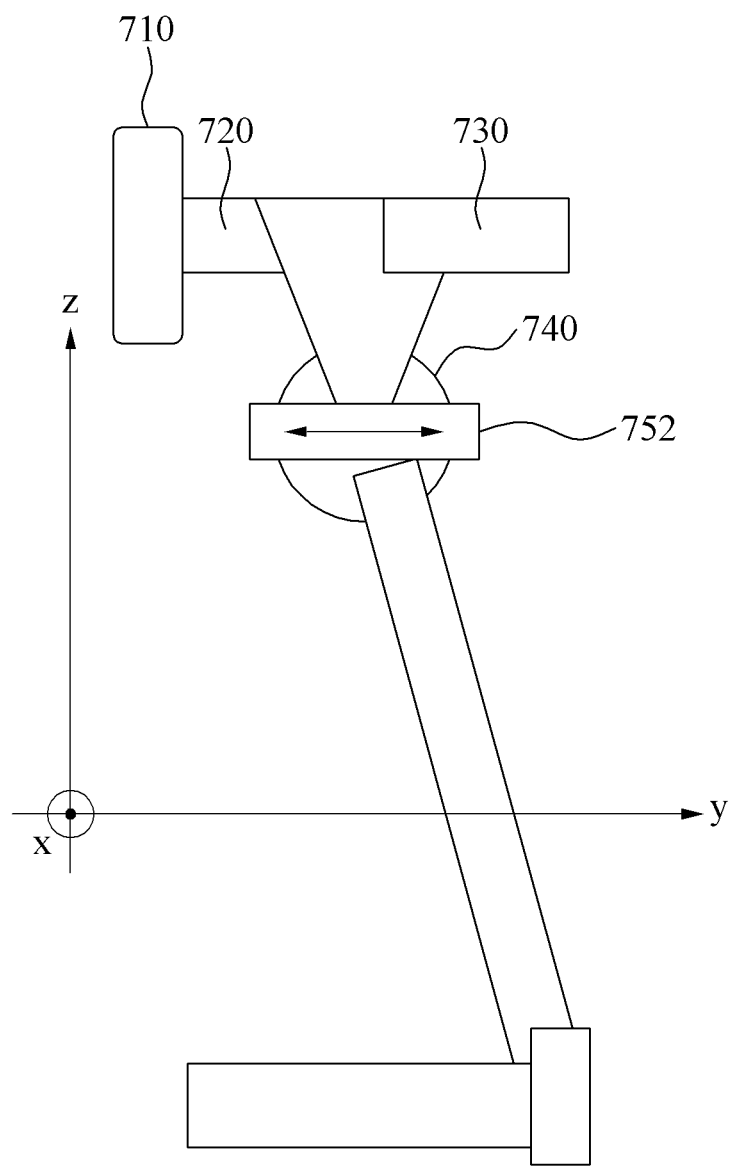
FIG. 7B is a side view of a wearable assistance apparatus for adjusting a position of a driving unit according to at least one example embodiment.

FIG. 7B is a side view of another example of a wearable assistance apparatus for adjusting a position of a driving unit.

Referring to FIG. 7B, the wearable assistance apparatus of FIG. 7B includes the back supporter 710, the waist frame 720, the waist wearing portion 730, the driving unit 740, and a second guide 752.

The second guide 752 is connected to the waist frame 720 and guides the driving unit 740 to linearly move in a desired (or, alternatively, a predetermined) direction. For example, the direction indicates a Y-axial direction (forward direction and backward direction) based on a user body. The driving unit 740 may have a degree of freedom of a movement from a forward direction to a backward direction through the second guide 752. Thus, the wearable assistance apparatus may adjust a position of a driving unit in the forward direction and the backward direction of the user corresponding to a thickness of hip or a thickness of thigh of the user.

Figure 7C:
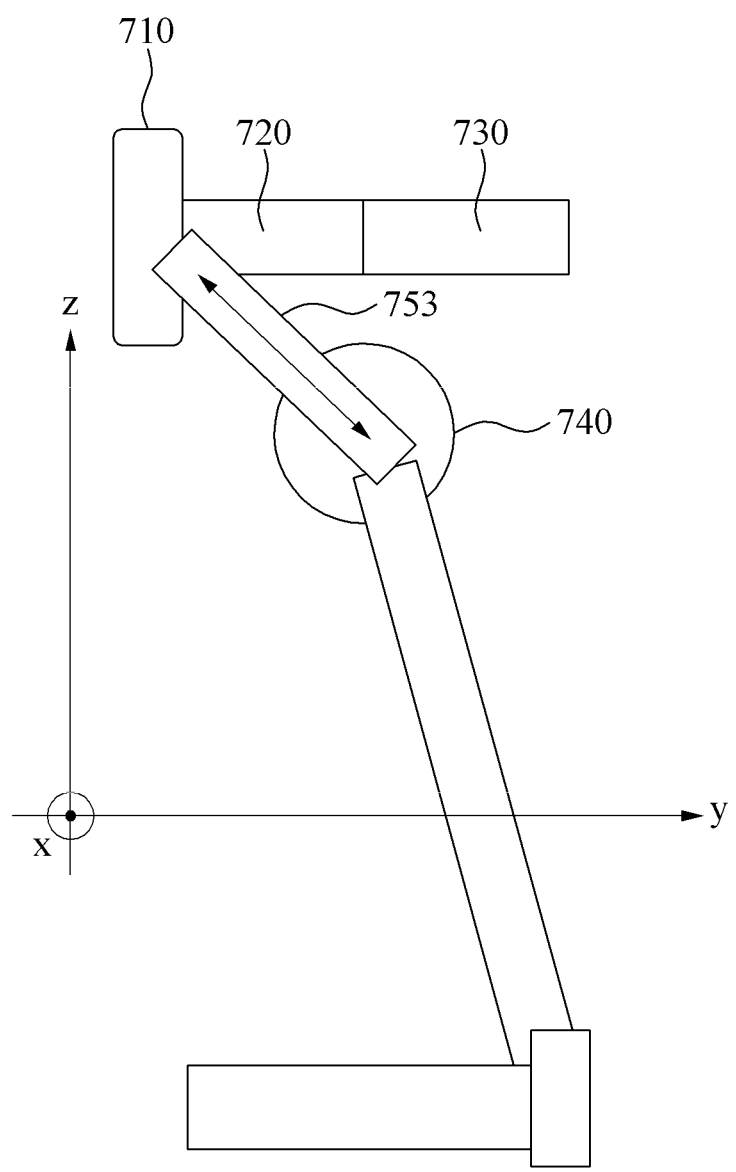
FIG. 7C is a side view of a wearable assistance apparatus for adjusting a position of a driving unit according to at least one example embodiment.

FIG. 7C is a side view of still another example of a wearable assistance apparatus for adjusting a position of a driving unit.

Referring to FIG. 7C, the wearable assistance apparatus of FIG. 7C includes the back supporter 710, the waist frame 720, the waist wearing portion 730, the driving unit 740, and a third guide 753.

The third guide 753 is connected to the waist frame 720 and guides the driving unit 740 to linearly move in a desired (or, alternatively, a predetermined) direction. For example, the direction indicates a direction present on a plane perpendicular to an axial direction of a rotation power generated by the driving unit 740. The driving unit 740 may have a single-degree of freedom in a direction from a center direction of the back supporter 710 to pass through a center of the driving unit 740 through the third guide 753 corresponding to a size of user body. Thus, the wearable assistance apparatus may adjust a position of a driving unit on a Y-Z plane corresponding to the size of user body.

Figure 8A:
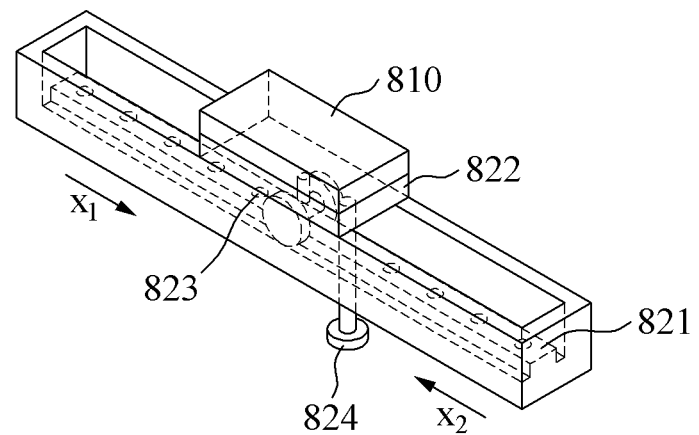
FIG. 8A illustrates a guide connected to a driving unit according to at least one example embodiment.

FIG. 8A illustrates a guide connected to a driving unit according to at least one example embodiment.

Referring to FIG. 8A, the guide includes a rail 821 extendable along a desired (or, alternatively, a predetermined) direction, a moving member 822 to be in contact with a driving unit 810 to move along the rail 821, at least one hole 823 disposed on the rail 821 at a desired (or, alternatively, a predetermined) distance, and a pin 824 connected to the moving member 822 and inserted into any one of the at least one hole 823.

The moving member 822 includes a wheel rotating in contact with the rail 821, and the driving unit 810 is connected to an upper end of the moving member 822. A wearable assistance apparatus may adjust a position of the driving unit 810 by moving the moving member 822 along the rail 821.

For example, the rail 821 of the guide is provided along a Z-axial direction, that is, a height direction of a user. In this example, gravity is applied to the guide and the driving unit 810 in a vertical direction in which a degree of freedom of movement exists. Thus, the user or a protector of the user using the wearable assistance apparatus may insert the pin 824 included in the guide into any one of the at least one hole 823. In response to the pin 824 being inserted into the hole 823, the wearable assistance apparatus may fix the driving unit 810 at a desired height. Thus, the wearable assistance apparatus may accurately adjust the position of the driving unit 810 in the height direction of the user.

Figure 8B:
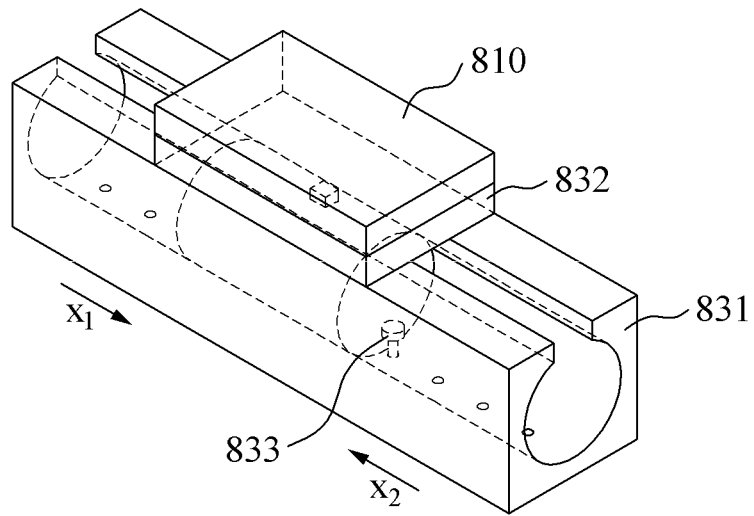
FIG. 8B illustrates a guide connected to a driving unit according to at least one example embodiment.

FIG. 8B illustrates a guide connected to a driving unit according to at least one example embodiment.

Referring to FIG. 8B, the guide includes a guide block 831 to form a movement path along a desired (or, alternatively, a predetermined) direction, a moving member 832 connected to the driving unit 810 to move along the movement path, and a stopper 833 disposed on the movement path. The moving member 832 is inserted on the movement path formed by the guide block 831, and the driving unit 810 is connected to an upper end of the moving member 832. The moving member 832 may move within a range of the guide block 831 to guide a linear movement of the driving unit 810.

The guide block 831 includes a plurality of holes disposed at a desired (or, alternatively, a predetermined) distance. The stopper 833 is inserted into any one of the holes and fixes the driving unit 810 at a predetermined position. For example, the stopper 833 is provided in a form of a screw bolt and inserted into any one of the holes such that the moving member 832 is prevented from being moved on the movement path.

The user or the protector of the user of the wearable assistance apparatus may insert the stopper 833 into any one of the holes. Based on the above-described operations, the wearable assistance apparatus may fix a rotation axis of the driving unit 810 based on a body size of the user.

Figure 9A:
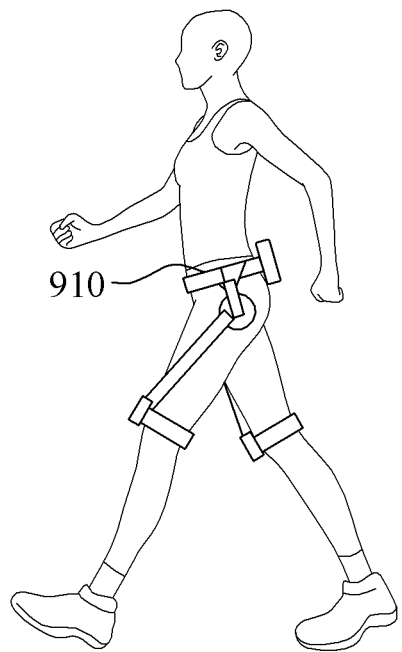
FIGS. 9A through 9C illustrate a wearable assistance apparatus in contact with various target portions a guide connected to a driving unit according to at least one example embodiment.
Figure 9B:
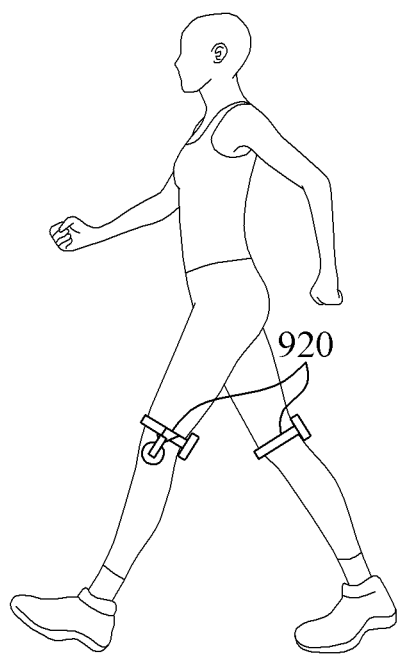
Figure 9C:
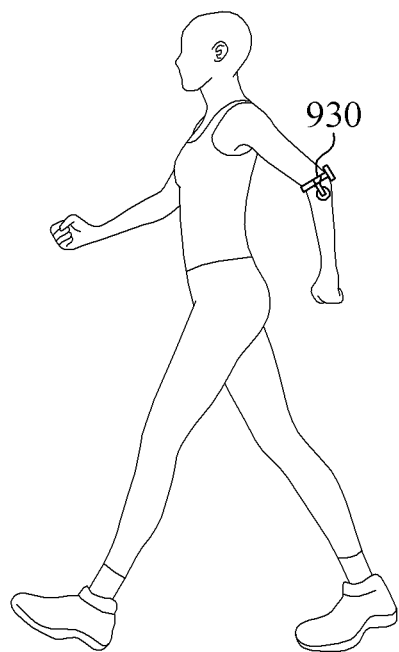

FIGS. 9A through 9C illustrate a wearable assistance apparatus in contact with various target portions a guide connected to a driving unit according to at least one example embodiment. The wearable assistance apparatus is in contact with various target portions of a user, and provides an assistance power for the user.

Referring to FIG. 9A, FIG. 9A illustrates an example in which a first wearable assistance apparatus 910 is provided as a hip-joint assistance apparatus. The first wearable assistance apparatus 910 includes a back supporter and a frame adhering to the user in a waist-width direction.

Referring to FIG. 9B, FIG. 9B illustrates an example in which a second wearable assistance apparatus 920 is provided as a knee assistance apparatus. A wearing portion of the second wearable assistance apparatus 920 may be provided in a form in which the knee assistance apparatus is bound to a knee of user.

Referring to FIG. 9C, FIG. 9C illustrates an example in which a third wearable assistance apparatus 930 is provided as an elbow assistance apparatus. In addition, a wearing portion of the third wearable assistance apparatus 930 is provided in a form in which the elbow assistance apparatus is bound to an elbow of user.

However, FIGS. 9A to 9C are only examples. A wearable assistance apparatus may also assist movements of other joints of user body.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magnetooptical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A wearable assistance apparatus, comprising:
   a first frame configured to transfer a first power to assist a user, the first power being generated by a first driving device attached to the first frame;
   a second frame configured to transfer a second power to assist the user, the second power being generated by a second driving device attached to the second frame, the second driving device being a separate driving device from the first driving device;
   a first pull portion configured to urge the second frame towards the user in response to the first pull portion being pulled in a first direction;
   a second pull portion configured to urge the first frame towards the user in response to the second pull portion being pulled in a second direction; and
   a guide configured to guide at least one of the first frame and the second frame to move linearly in a set direction,
      wherein each of the first frame and the second frame include a plurality of holes therein, and
      the first pull portion is threaded through the plurality of holes in the first frame and connected to the second pull portion and the second pull portion is threaded through the plurality of holes in the second frame and connected to the first pull portion such that the first pull portion and the second pull portion form a cross-connection structure in which the first pull portion pulls the second frame including the second driving device in the first direction in response to the first power and the second pull portion pulls the first frame including the first driving device in the second direction in response to the second power.

2. The wearable assistance apparatus of claim 1, further comprising:
   the first driving device configured to generate the first power,
   the second driving device configured to generate the second power; and
   a supporter configured to contact a target portion of the user to support the user.

3. The wearable assistance apparatus of claim 2, wherein a set direction is orthogonal to a direction of the first power and the second power.

4. The wearable assistance apparatus of claim 1, wherein the guide comprises:
   a rail extendable along a set direction such that the at least one of the first frame and the second frame is configured to move along the rail.

5. The wearable assistance apparatus of claim 1, wherein the guide comprises:
   a guide block that forms a movement path along a set direction such that the at least one of the first frame and the second frame is configured to move along the movement path.

6. The wearable assistance apparatus of claim 1, further comprising:
   a fastening portion configured to fix the first pull portion to the second pull portion such that the first frame and the second frame are fixed to a set target portion of the user in response to the first pull portion being fastened to the second pull portion.

7. The wearable assistance apparatus of claim 1, wherein the first frame is connected to a first end of the second pull portion, and the second frame is connected to a first end of the first pull portion.

8. The wearable assistance apparatus of claim 1, wherein
   the first pull portion is configured to pass through the first hollow portion to transfer the first power to move the second frame, and
   the second pull portion is configured to pass through the second hollow portion to transfer the second power to move the first frame.

9. A wearable assistance apparatus, comprising:
   a back supporter configured to contact a back of a user to support the user;
   a driving device configured to generate a power to assist movement of a hip joint of the user;
   a waist frame configured to fasten to a waist of the user, and to transfer the power to the back supporter; and
   a guide connected to the waist frame, the guide configured to guide movement of the driving device to adjust a distance between the driving device and the waist frame such that the driving device corresponds to the hip joint of the user, the guide including,
      a rail extendable vertically such that the driving device is configured to move along the rail, and
      a movable member connected to the driving device, the movable member including a wheel configured to directly contact and rotate about the rail to move the movable member along the rail.

10. The wearable assistance apparatus of claim 9, wherein the guide further comprises:
   at least one hole on the rail at a set distance; and
   a pin connected to the movable member and inserted into any one of the at least one hole to fix the driving device.

* * * * *